United States Patent
Kriesel

(10) Patent No.: US 6,245,041 B1
(45) Date of Patent: Jun. 12, 2001

(54) FLUID DISPENSER WITH FILL ADAPTER

(75) Inventor: Marshall S. Kriesel, Saint Paul, MN (US)

(73) Assignee: Science Incorporated, Bloomington, MN (US)

( * ) Notice: Subject to any disclaimer, the term of this patent is extended or adjusted under 35 U.S.C. 154(b) by 0 days.

(21) Appl. No.: 09/561,786

(22) Filed: May 1, 2000

Related U.S. Application Data

(63) Continuation-in-part of application No. 09/329,840, filed on Jun. 10, 1999, now Pat. No. 6,090,071, which is a continuation-in-part of application No. 09/165,709, filed on Oct. 2, 1998, now Pat. No. 5,980,489, which is a continuation-in-part of application No. 08/729,326, filed on Oct. 15, 1996, now Pat. No. 5,873,857, which is a continuation-in-part of application No. 08/577,496, filed on Dec. 22, 1995, now Pat. No. 5,700,244, which is a continuation-in-part of application No. 08/192,031, filed on Feb. 3, 1994, now Pat. No. 5,484,415, which is a continuation-in-part of application No. 08/156,685, filed on Nov. 22, 1993, now Pat. No. 5,433,709, which is a continuation-in-part of application No. 08/053,723, filed on Apr. 26, 1993, now Pat. No. 5,354,278, which is a continuation-in-part of application No. 07/870,521, filed on Apr. 17, 1992, now Pat. No. 5,263,940.

(51) Int. Cl.[7] .................................................. A61M 37/00
(52) U.S. Cl. .............................................................. 604/131
(58) Field of Search .................................... 604/131, 132, 604/133, 151, 153, 190, 246–248, 232–236, 189, 80–83

Primary Examiner—Manuel Mendez
(74) Attorney, Agent, or Firm—James E. Brunton, Esq.

(57) ABSTRACT

An elastomeric bladder stored energy type infusion apparatus that can be filled with a medicinal fluid and, after being filled, can efficiently deliver the medicinal fluid to the patient at a selected rate. The apparatus includes a delivery component for delivering medicinal fluid to the patient and a fill component that can expeditiously be used to fill the fluid reservoir of the delivery component in the field.

23 Claims, 7 Drawing Sheets

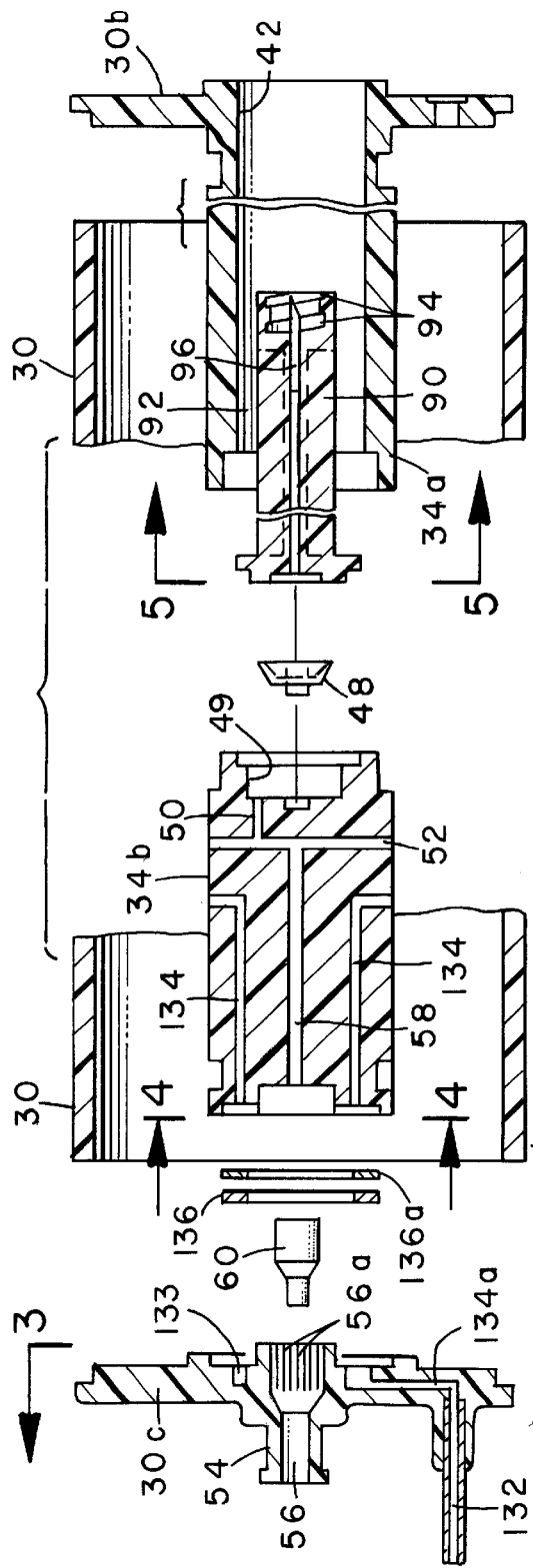
FIG. 2
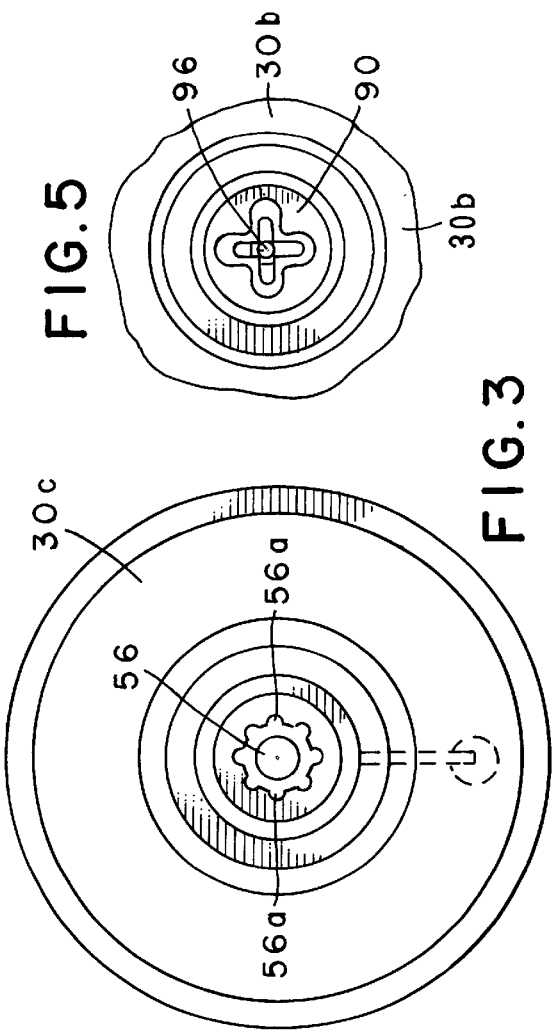
FIG. 3
FIG. 5
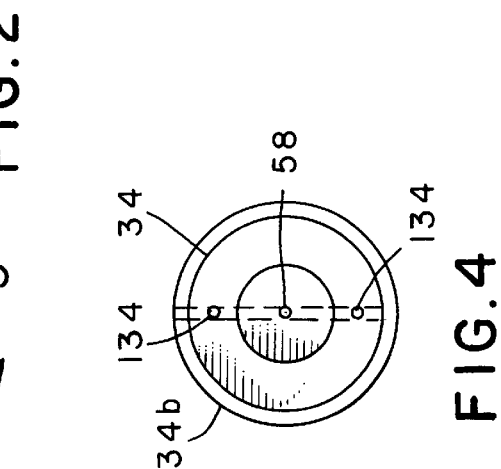
FIG. 4

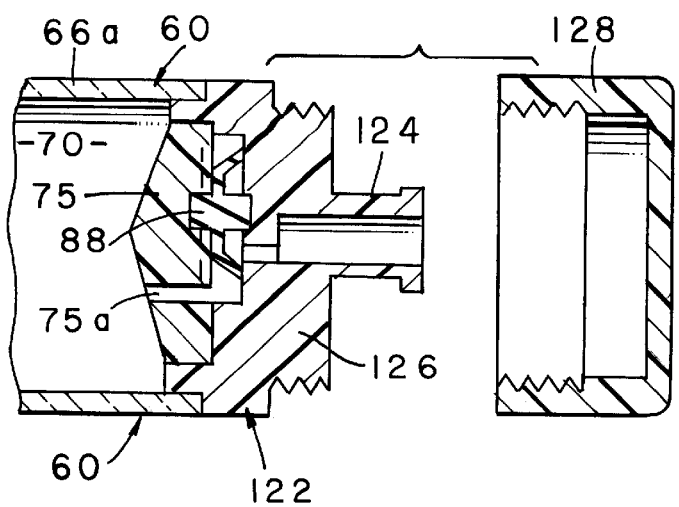
FIG. 8
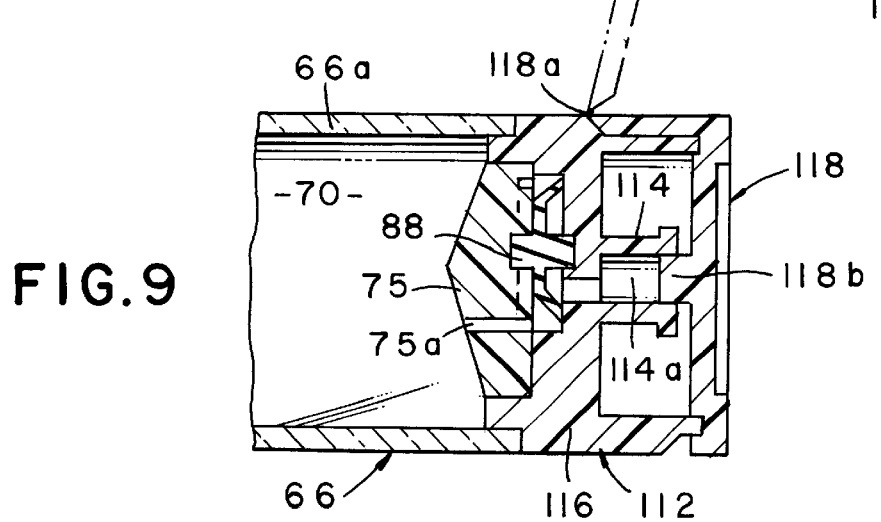
FIG. 9
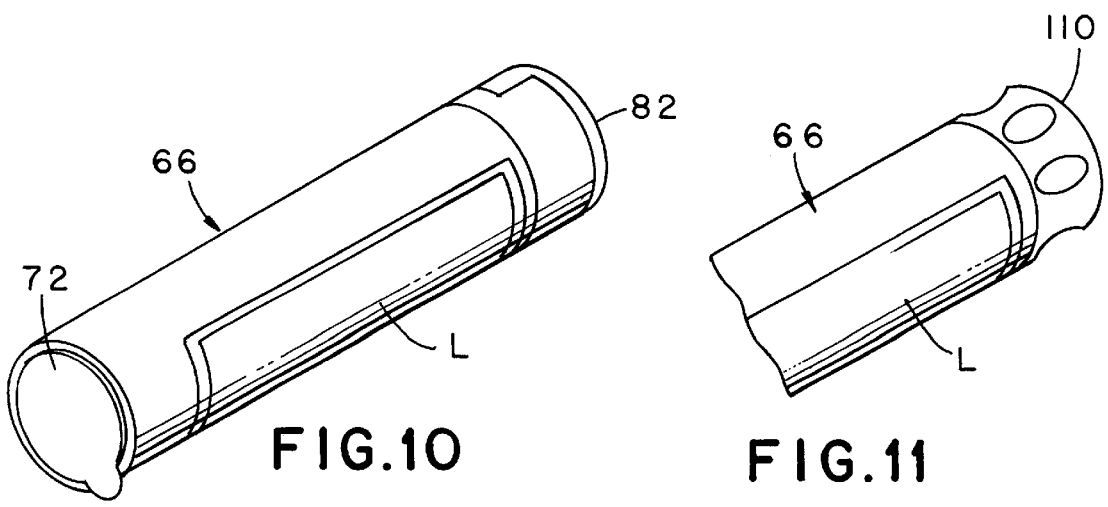
FIG. 10
FIG. 11

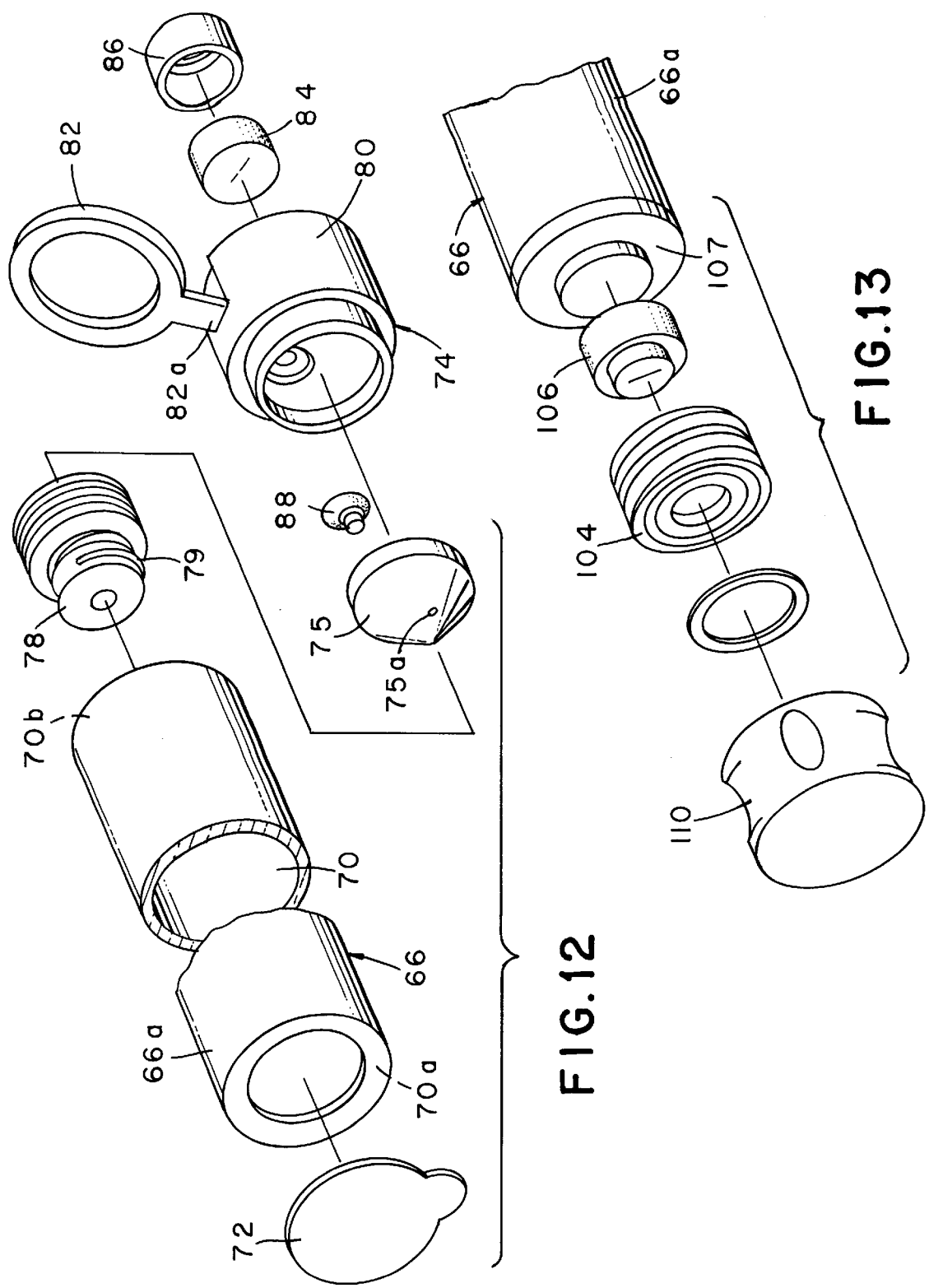

FLUID DISPENSER WITH FILL ADAPTER

BACKGROUND OF THE INVENTION

This is a Continuation-In-Part application of U.S. Ser. No. 09/329,840 filed Jun. 10, 1999 now U.S. Pat. No. 6,090,071, which is a Continuation-in-Part of U.S Ser. No. 09/165,709 filed Oct. 2, 1998 now U.S. Pat. No. 5,980,489, which is a Continuation-In-Part of U.S. Ser. No. 08/729,326 filed Oct. 15, 1996 and now issued into U.S. Pat. No. 5,873,857; which is a Continuation-In-Part of U.S. Ser. No. 08/577,496 filed Dec. 22, 1995 and now issued into U.S. Pat. No. 5,700,244; which is a Continuation-In-Part of U.S. Ser. No. 08/192,031 filed Feb. 3, 1994 and now issued into U.S. Pat. No. 5,484,415; which is a Continuation-In-Part of U.S. Ser. No. 08/156,685 filed Nov. 22, 1993 and now issued into U.S. Pat. No. 5,433,709; which is a Continuation-In-Part of U.S. Ser. No. 08/053,723 filed Apr. 26, 1993 and now issued into U.S. Pat. No. 5,354,278; which is a Continuation-In-Part of U.S. Ser. No. 07/870,521 filed Apr. 17, 1992 and now issued into U.S. Pat. No. 5,263,940.

FIELD OF THE INVENTION

The present invention relates generally to infusion devices. More particularly, the invention concerns an elastomeric bladder type infusion apparatus which is used for controllably delivering a beneficial agent to a patient. The device uniquely includes novel fill means for filling the reservoir of the infusion apparatus with the medicament to be delivered to the patient.

DISCUSSION OF THE PRIOR ART

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestresses the bladder in both the axial and radial directions when disposed therein, substantially filling the bladder in its unfilled state. The Hessel device also includes a one-way valve on the stress member which permits flow only in the direction of the interior of the bladder.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time.

One of the more advanced elastomeric bladder type devices ever developed is described in U.S. Pat. No. 5,354,278 issued to the present inventor. Because the present invention comprises an improvement to the devices disclosed in this latter patent, U.S. Pat. No. 5,354,278 is hereby incorporated by reference as though fully set forth herein. Another advanced elastomeric bladder type device is disclosed in U.S. Pat. No. 5,873,857 also issued to the present inventor. This patent is also incorporated by reference as though fully set forth herein.

Still another novel bladder type device having a unique filling means is disclosed in the U.S. patent application Ser. No. 09/329,840 filed by the present inventor on Jun. 10, 1999. This application is also incorporated by reference as though fully set forth herein.

None of the prior art devices known to applicant have the unique capability of the present invention for expeditiously filling the fluid reservoir of the delivery device in the field.

SUMMARY OF THE INVENTION

It is an object of the present invention to provide an elastomeric bladder, stored energy type infusion apparatus that can be filled in the field with a medicinal fluid and after being filled, can efficiently deliver a precise volume of the medicinal fluid to the patient. More particularly, it is an object of the invention to provide an infusion device of the aforementioned character which includes a novel filling means which can expeditiously be used in the field by a caregiver or physician.

Another object of the invention is to provide an apparatus of the aforementioned character which includes a delivery component and a filling component which can be operably interconnected with the delivery component to enable expeditious filling in the field of the fluid reservoir of the delivery component. More particularly, the novel filling component permits the pharmacist to aseptically fill the container under patient-specific-variable volume and concentration of medicament. In this way, body mass index requirements can be met for selected agents as, for example, immuno- and chemo-therapeutic agents.

Another object of the invention is to provide an apparatus as described in the preceding paragraph in which the filling component comprises a container having a fluid chamber that is accessible via either a septum that is sealably connected to the container or via a luer type connector.

Still another object of the invention is to provide a device of the character described in the preceding paragraphs which is highly reliable, inexpensive to produce in quantity, and easy to use in the home care environment.

BRIEF DESCRIPTION OF THE DRAWINGS

FIG. 2 is an enlarged, cross-sectional exploded view of the fluid delivery component of the apparatus shown in FIG. 1.

FIG. 3 is a view taken along lines 3—3 of FIG. 2.

FIG. 4 is a view taken along lines 4—4 of FIG. 2.

FIG. 5 is a view taken along lines 5—5 of FIG. 2.

FIG. 8 is a fragmentary, cross-sectional view of still another form of the field fill component of the apparatus of the invention showing the closure cap separated from the body portion.

FIG. 9 is a fragmentary, cross-sectional view similar to FIG. 1, but showing in phantom the closure panel in an open configuration.

FIG. 10 is a generally perspective view of one form of the field fill component of the apparatus of the invention.

FIG. 11 is a generally perspective, fragmentary view of an alternate form of the field fill component of the apparatus of the invention.

FIG. 12 is a generally perspective exploded view of the field fill component of the invention shown in FIG. 10.

FIG. 13 is a generally perspective, fragmentary exploded view of the field fill component shown in FIG. 11.

DESCRIPTION OF ONE FORM OF THE INVENTION

Figure 1:
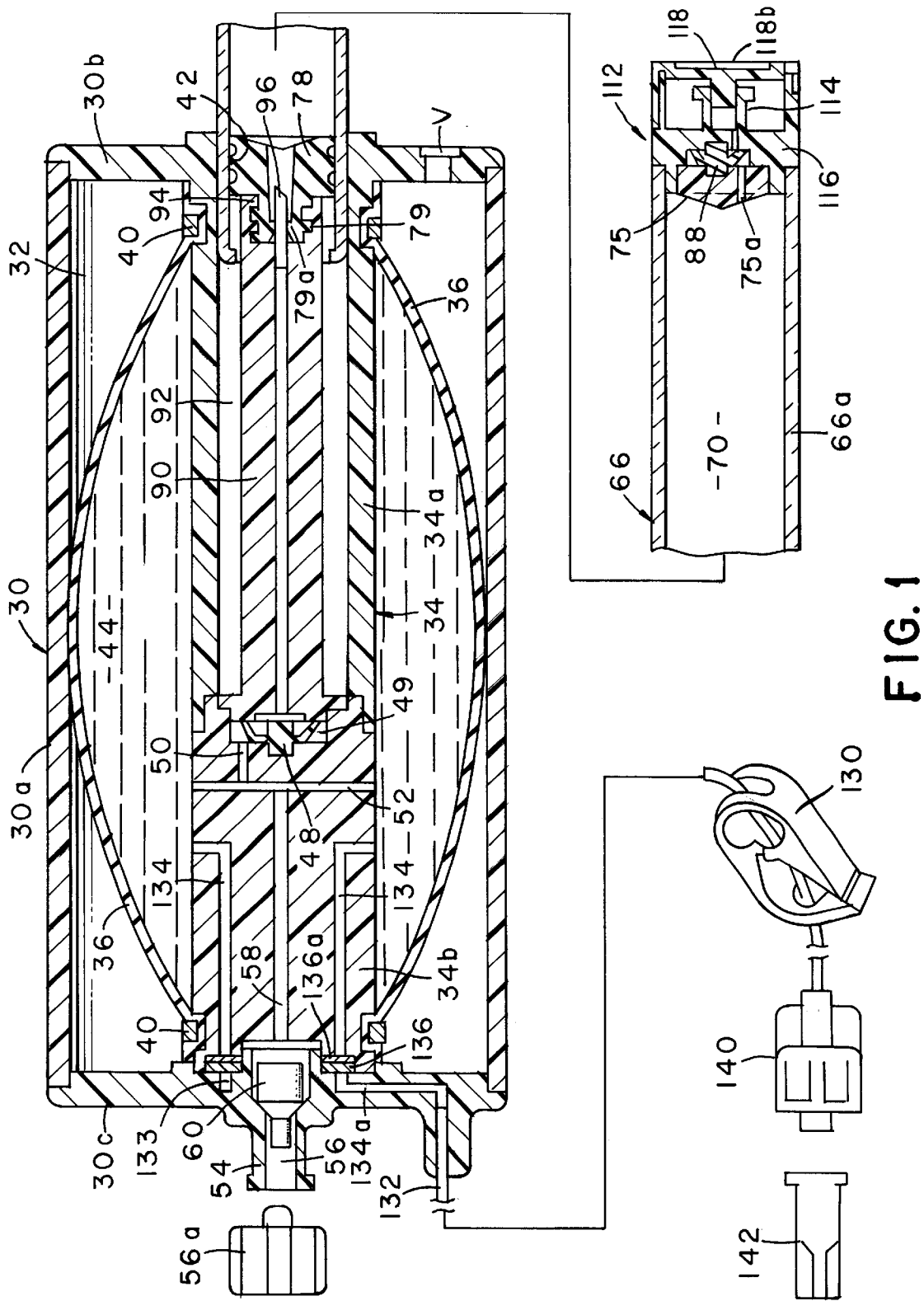
FIG. 1 is a side-elevational, cross-sectional view of one form of the fluid delivery apparatus of the present invention.
Figure 6:
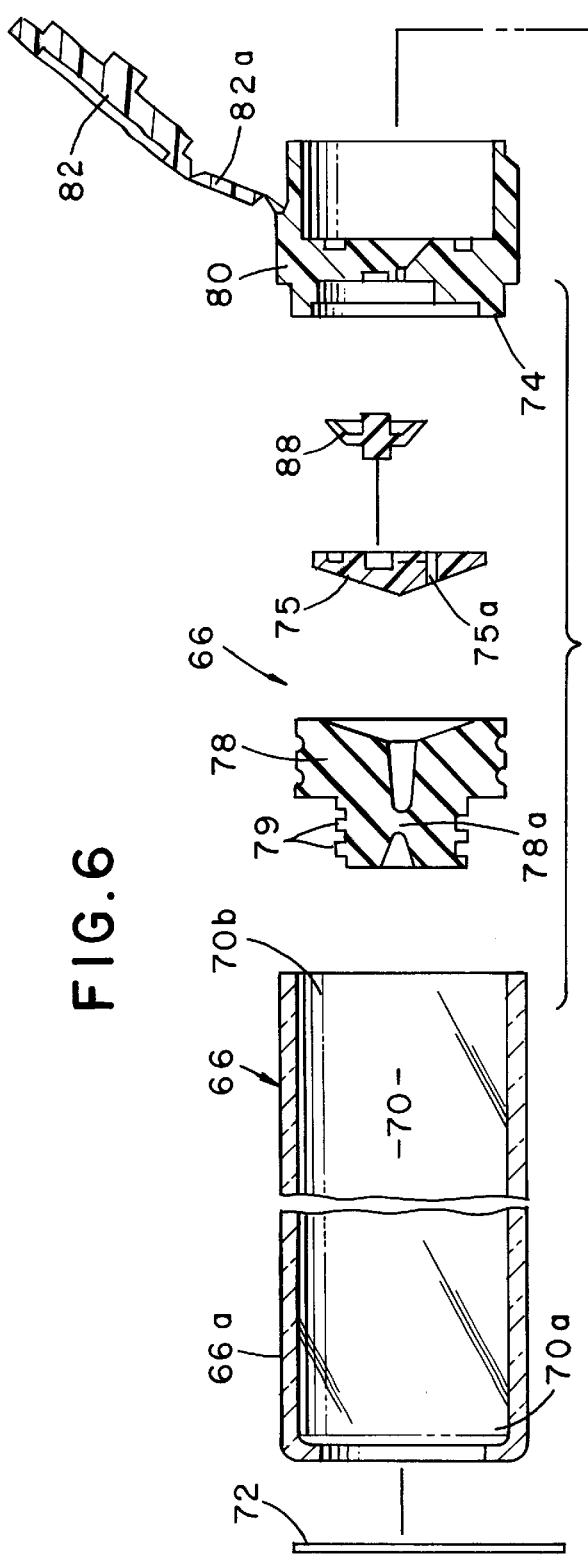
FIG. 6 is an enlarged, exploded cross-sectional view of one form of the field fill component of the apparatus of the invention.

Referring to the drawings and particularly to FIG. 1, the fluid dispenser apparatus of one form of the present invention can be seen to comprise an elongated housing 30 having a first internal chamber 32, a support 34 disposed within internal chamber 32 and extending longitudinally of the housing 30, and a generally cylindrically shaped, elongated elastomeric member 36.

Housing 30 comprises a cylindrically shaped central portion 30a and inlet and outlet end closure portions 30b and 30c respectively. Central section 30a and end portions 30b and 30c can be interconnected by any suitable means such as adhesive bonding or an appropriate sonic weldment. Elastomeric member 36 is securely affixed proximate its ends to support 34 by means of suitable ring clamps 40, such as self-locking plastic panduit strips.

As best seen by referring to FIG. 2, support 34 is constructed in two parts 34a and 34b which are suitably interconnected in the manner shown in the drawings. Part 34a is provided with a receiving chamber 42 which, in a manner presently to be described, telescopically receives a portion of the first fill means of the invention for filling a reservoir 44 with a selected fluid. Reservoir 44 is formed by elastomeric member 36 and the central portion of support 34 (FIG. 1). Valve means, shown here as a check valve 48, is disposed within a chamber 49 and functions to permit fluid flow toward reservoir 44, but blocks fluid flow in the opposite direction.

Support 34 is provided with an inlet passageway 50 which communicates with a transversely extending passageway 52. A second fill means, which includes a luer connector 54 having a fluid passageway 56, is operably interconnected with closure portion 30c. When the second fill means of the apparatus is not in use, passageway 56 is suitably closed by a closure cap 56a (FIG. 1). As shown in FIG. 1, passageway 56 is in communication with transverse passageway 52 via a passageway 58 and a first flow control means here provided in the form of a conventional check valve 60. As will presently be discussed, the second fill means can also be used to fill or partially fill reservoir 44 with a selected fluid.

Provided at the opposite end of the assemblage from luer-like connector 54 is the important first fill means of this latest form of the invention for introducing a medicament into reservoir 44. Turning to FIGS. 6, 12, 14 and 15, this novel means of the invention can be seen to include a container subassembly 66 that comprises a container, or vial portion 66a having a fluid chamber 70 for containing an injectable fluid "F". Fluid chamber 70 is provided with first and second open ends 70a and 70b. First end 70a is closed by a porous, self-venting closure peel away 72. Second open end 70b is sealably closed by closure means here provided in the form of a closure subassembly 74. Displacement means, here shown as a plunger 78, is telescopically movable within chamber 70 of container subassembly 66 in the manner indicated in the drawings.

Figure 14:
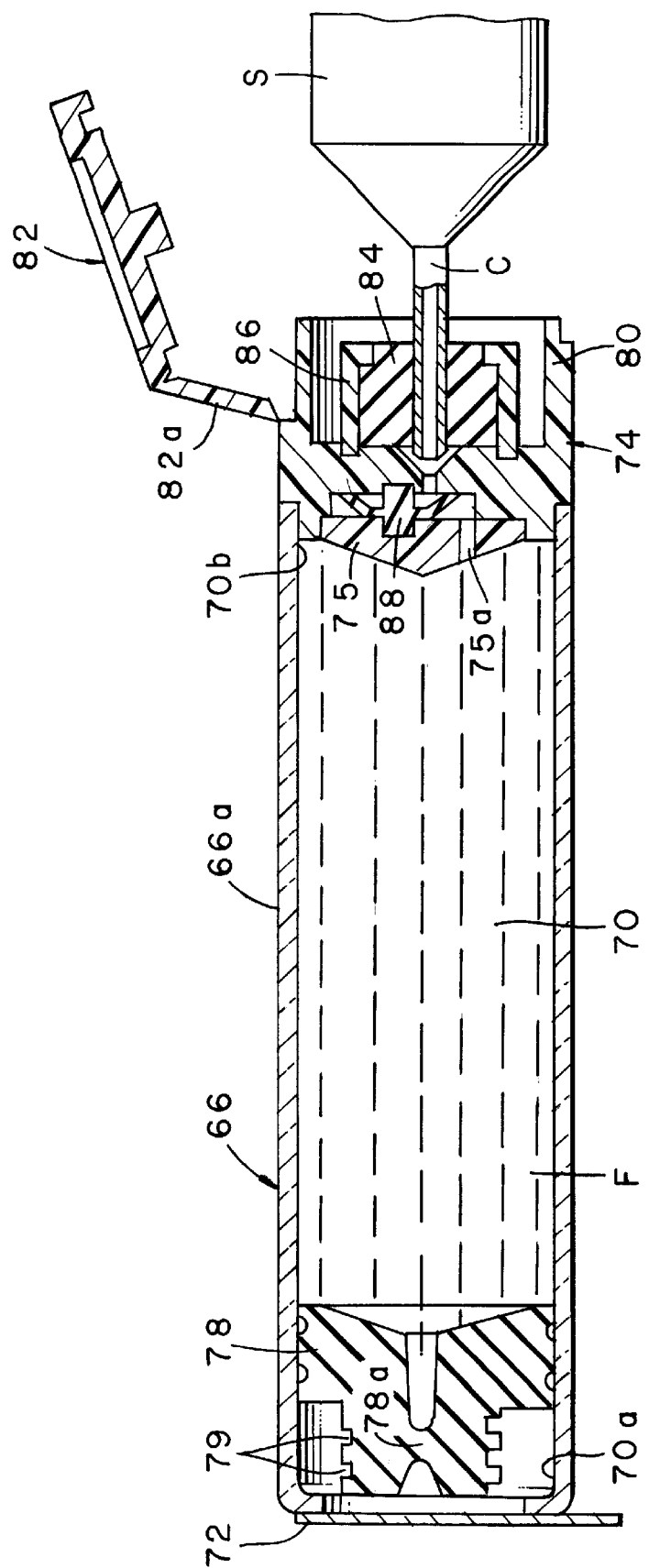
FIG. 14 is a cross-sectional view of one form of the field fill component of the invention illustrating the manner in which the fluid reservoir of the component is filled with the fluid to be delivered to the patient.
Figure 15:
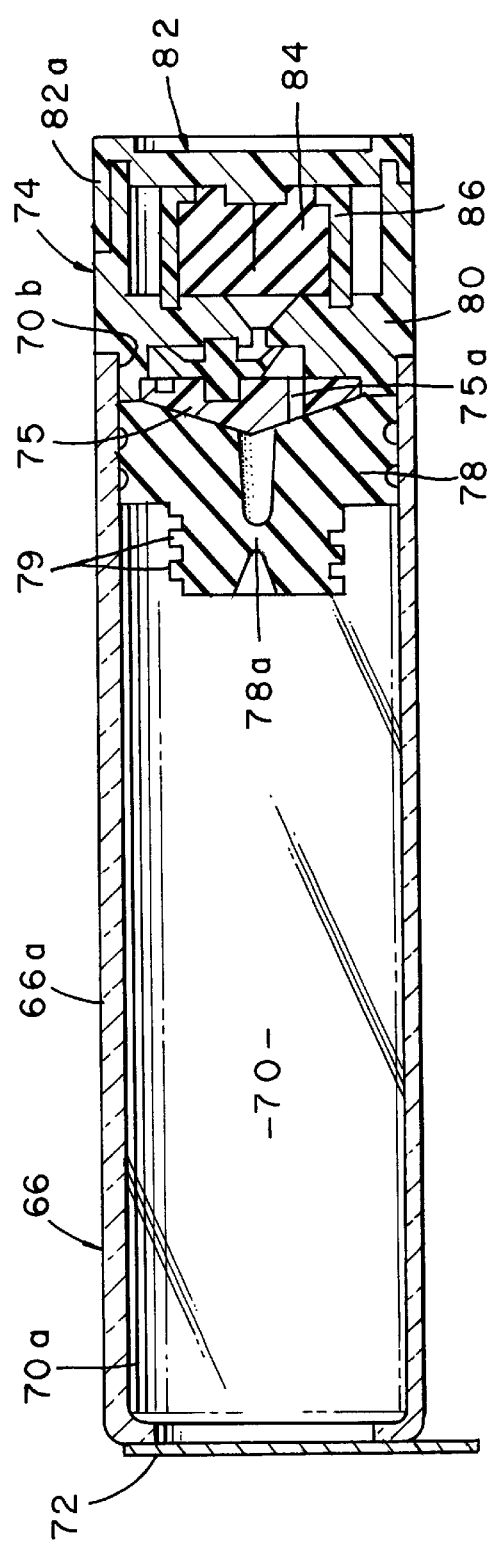
FIG. 15 is a cross-sectional view of the field-fill component of the invention as it appears prior to the reservoir filling step.
Figure 16:
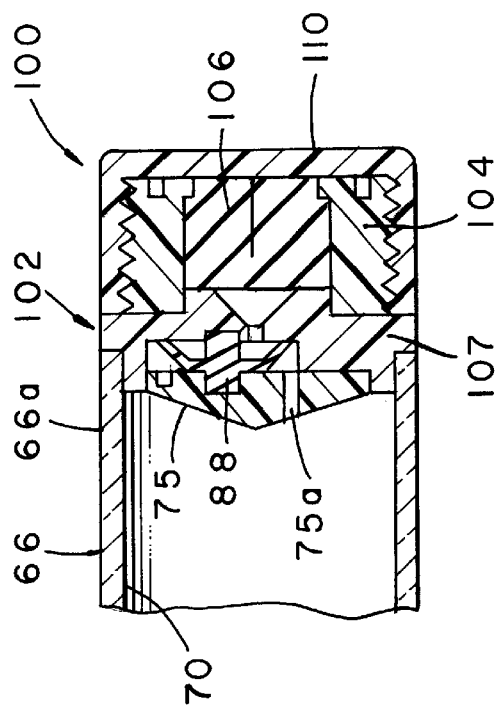
FIG. 16 is a fragmentary cross-sectional view of an alternate form of the field fill apparatus of the invention from that shown in FIG. 15.

Closure subassembly 74 is connected to container 66a in the manner shown in FIG. 15 and comprises a closure housing 80 and a closure panel 82 that is hingedly connected to housing 80 for movement between a closed position shown in FIG. 15 and an open position shown in FIG. 14. Also comprising a part of closure subassembly 74 is connector means for interconnecting fluid chamber 70 with a source of medicinal fluid. In the form of the invention shown in FIGS. 14 and 15 this connector means comprises a slit septum 84 which is sealably mounted within a collar 86 which is, in turn, connected to housing 80. Slit septum 84 is accessible by lifting hingeably mounted end panel 82 in the manner shown in FIG. 14. Panel 82 is connected to housing 80 by means of a living hinge 82a. When panel 82 is lifted in the manner shown in FIG. 14, slit septum 84 can be pierced by a blunt end cannula "C" of a conventional syringe assembly "S" or like filling means. As chamber 70 is filled with fluid, plunger 78 will be moved from the first position shown in FIG. 15 to the second position shown in FIG. 14. Also forming a part of closure subassembly 74 is valve means for controlling fluid flow toward to chamber 70 of container 66a. In the present form of the invention this valve means comprises a conventional umbrella check valve 88. Check valve 88 is held in position within a cavity defined through the cooperation of housing 80 and a disk-like member 75 having a fluid passageway 75a. Disk-like member 75 includes an external, cooperating geometry that is closely positioned to the proximal portion of plunger 78 in the manner shown in FIG. 15.

Following aseptic filling of chamber 70 in the manner shown in FIG. 14, and removal of self-venting peel-away closure 72, container subassembly 66 can be telescopically inserted into receiving chamber 42 of support 34 and moved from a first extended position into a second, fluid filling position. In this regard, support 34 also includes pusher means, shown here as an elongated pusher member 90 (FIG. 2), which functions to move plunger 78 longitudinally of fluid chamber 70 of the container subassembly upon urging of the container subassembly into support 34.

As indicated in FIG. 1, pusher member 90 is radially spaced from the interior wall of receiving chamber 42 so as to define a longitudinally extending annular space 92. With this construction, during the mating of the first fill means with the fluid delivery component, the outer wall of vial 66a is closely received within annular space 92 as the container subassembly is moved inwardly or forwardly of the device housing. It is to be observed that when the container subassembly is originally mated with the delivery component in the manner shown in FIG. 1, threads 79 provided on plunger 78 will mate with internal threads 94 provided on pusher member 90 (FIGS. 1 and 2). Upon subsequent relative rotation of the components, a pierceable wall 78a of plunger 78 of container subassembly 66 will move into piercing engagement with a hollow cannula 96 that is disposed centrally of pusher member 90. Once the hollow cannula 96 has pierced the plunger 78, the fluid flow path between the hollow cannula 96 and the fluid reservoir 44 of the apparatus is thus created via check valve 48, via passageway 50 and via passageway 52, the reservoir can be filled by an inward movement of the container subassembly. As the container subassembly moves inwardly, pusher member 90 will move plunger 78 inwardly of container 66a causing fluid contained within chamber 70 of the container to flow through hollow cannula 96, past umbrella check valve 48, into passageway 50, into passageway 52 and finally into fluid reservoir 44 (FIG. 1). As fluid reservoir 44 is filled, air trapped within housing 30 is vented to atmosphere via vent "V" (FIG. 1).

As will be discussed more fully hereinafter, in certain instances, reservoir 44 may be prefilled using the second fill means of the invention. Using the second fill means, the reservoir can be filled with selected beneficial agents contained in vial subassembly 66. During the filling step, these agents will be controllably intermixed as the adapter subassembly is moved inwardly. It is to be understood that if desired cannula 96 can also be a blunt end cannula and wall 78a can be constructed with a slit portion to accept the blunt end cannula.

Figure 7:
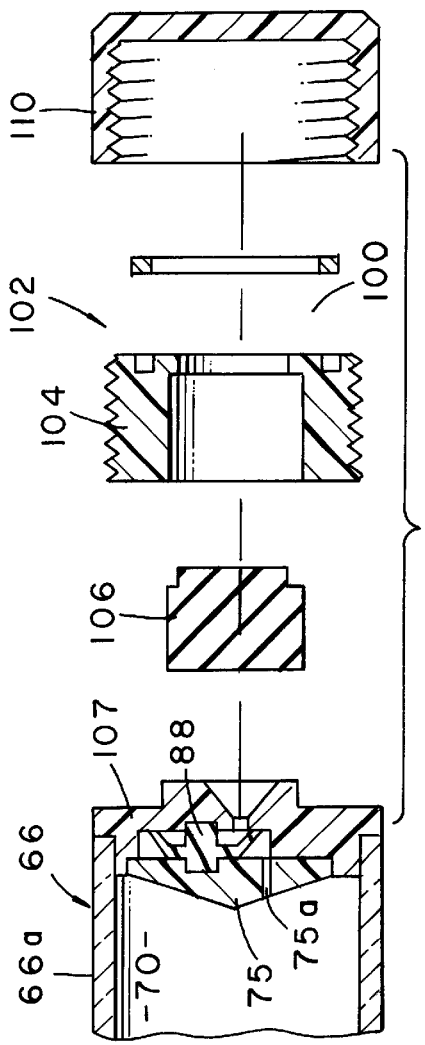
FIG. 7 is an exploded, fragmentary cross-sectional view of an alternate form of the field fill component of the apparatus of the invention.

Referring next to FIGS. 7, 11, 13 and 16, an alternative form of first fill means of the invention is there illustrated. This form of the invention is similar in many respects to that previously described and like numerals are used in these figures to identify the like components shown in FIGS. 14 and 15. Turning particularly to FIG. 7, it is to be noted that this alternate form of first fill means includes a container 66a having a fluid chamber 70. Container assembly 66 is preferably provided with a medicament label "L" Connected to container 66a is an alternative form of closure subassembly here generally designated by the numeral 100. Closure subassembly 100 is connected to container 66a in the manner shown in FIG. 16 and includes a closure housing 102. Closure housing 102 comprises an externally threaded septum housing 104 within which a slit septum 106 is sealably mounted. Septum housing 104 is connected to a connector member 107 which, in turn, is connected to container 66a. Surrounding septum housing 104 and disposed in an abutting relationship with member 107 is an end closure 110. End closure is internally threaded so that it can be threadably interconnected with septum housing 104 in the manner illustrated in FIG. 16. Access to septum 106 during the filling operation is accomplished by threadably removing end cap 110 so as to enable piercing of slit septum 106 by the cannula of a syringe or like filling component.

Considering next FIGS. 1 and 9, still another form of first fill means of the invention is there illustrated. Once again, this latest embodiment is similar in many respects to those previously described, and like numerals are used to identify like components. As before, this latest embodiment includes a container 66a having a fluid chamber 70. Connected to container 66a in the manner shown in FIG. 9 is a closure subassembly 112. Subassembly 112, along with member 75, supports check valve 88 in a manner best seen in FIG. 9. As indicated in FIG. 8, in this latest form of the first fill means of the invention the slit septum has been replaced by a luer-like connector 114 which extends rearwardly of the fill assembly in the manner illustrated in FIG. 9.

Hingedly connected to a closure housing 116, which forms a part of closure subassembly 112, is a closure panel 118. Closure panel 118 includes a living hinge segment 118a and a central protuberance 118b that is sealably received within passageway 114a of luer-like protuberance 114 when the closure panel is in the closed position. More particularly, the closure panel 118 is moved from the position shown in the phantom lines in FIG. 9 to the position shown in the solid lines, protuberance 118b is sealably received within opening 114a of luer-like protuberance 114. To fill reservoir 70 of this latest embodiment of the invention, panel 118 is moved to the open position shown in the phantom lines in FIG. 9 so as to expose the luer-like protuberance 114. This done, either a suitable syringe connector or a conventional female luer connector can be interconnected with protuberance 114 so that fluid from an external source (not shown) can be used to fill chamber 70 via check valve 88 and passageway 75a.

Turning next FIG. 8, yet another form of first fill means of the invention is there illustrated. This latest embodiment is similar in many respects to that shown in FIG. 9 and like numerals are used to identify like components. As before, this latest embodiment includes a container 66a having a fluid chamber 70. Connected to container 66a in the manner shown in FIG. 8 is a closure subassembly 122. Subassembly 122, along with member 75, supports check valve 88 in a manner shown in FIG. 8. In this latest form of the first fill means of the invention, the slit septum has once again been replaced by a luer-like connector 124 which extends rearwardly of the fill assembly in the manner shown in FIG. 8.

Threadably connected to closure housing 126, which forms a part of closure subassembly 122, is a threaded closure cap 128. To fill reservoir 70 of this latest embodiment of the invention, cap 128 is threadably removed from closure housing 126 so as to expose the luer-like protuberance 124. This done, either a suitable syringe connector or a conventional female luer connector can be interconnected with protuberance 124 so that fluid from an external source (not shown) can be used to fill chamber 70 via check valve 88 and passageway 75a.

Once the reservoir has been filled, the apparatus will remain in this readied condition until the line clamp 130 provided on the delivery line 132 of the infusion means of the device is opened (FIG. 1). Once the line clamp is opened and the luer closure cap 142 is removed, the stored energy means or membrane 36 will tend to return to a less distended condition causing fluid to flow outwardly of the apparatus via outlet passageways 134 formed in support 34 and through the novel flow control means of the invention, here shown as an annular shaped porous flow control elements 136 and 136a (FIGS. 1 and 2). Flow control element 136a may comprise a filter element of a character well known to those skilled in the art. Flow control element 136 may comprise a porous fluid rate control member as, for example, a porous ceramic or a porous plastic. After flowing through elements 136 and 136a, the fluid will flow outwardly of the device via passageways 133 and 134a and the infusion line 132. Provided at the outboard end of the delivery line 132 is a luer connector 140 which is closed by a removable cap 142 (FIG. 1). Luer connector 140 can be suitably interconnected with a cannula or like means for infusing the medicinal fluid into the patient.

As previously mentioned, reservoir 44 can also be filled with the selected fluid using the second fill means of the invention which here comprises luer-like connector 54 and conventional check valve 60. This is accomplished by interconnecting with connector 54 an appropriate fill line having a luer connector that is matable with connector 54. The fill line can be interconnected with any desired source of fluid which may be a diluent or an appropriate beneficial agent. When check valve 60 is moved inwardly from its selected position by the fill assembly, fluid will bypass valve 60 via circumferentially spaced grooves 56a (FIG. 3) and into reservoir 44 via passageways 52 and 58. If reservoir 44 has been previously, partially filled with a fluid, the fluid introduced via the second fill means will thereupon thoroughly intermix with the fluid contained within the reservoir.

With regard to the various suitable materials that can be used to construct the various components of the fluid dispenser portion of the invention, attention should be directed to incorporated by reference U.S. Ser. No. 09/329,840 and U.S. Pat. Nos. 5,354,278 and 5,873,857. However, for present purposes it should be understood that materials suitable for the construction of the container subassembly may include glass, or plastics including polycarbonate, or acrylic for the container; butryl rubber, silicone or polyisoprene for the stopper; a composite material sold by DuPont under the name and style, Tyvek™ or porous polyethylene for the removable self-venting closure; polypropylene or nylon for the closure panel; polycarbonate, acrylic, polypropylene or nylon for the closure cap and an elastomer such as silicone rubber or polyisoprene for the septum.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid delivery apparatus having a fluid delivery passageway, said apparatus comprising:
   (a) an elongated housing having walls defining an internal chamber;
   (b) a support assembly connected to said housing and including an elongated body disposed within said internal chamber, said body having a receiving chamber, an inlet passageway and an outlet passageway in communication with said fluid delivery passageway;
   (c) an elongated tubular shaped elastomeric member connected proximate its ends to said elongated body, said elastomeric member having a central portion disposed within said internal chamber of said housing and overlaying said inlet and outlet passageways, said central portion of said elastomeric member being distendable by fluid flowing through said first fluid passageway from a first position in proximity with said support to a second position to form a fluid reservoir;
   (d) fill means interconnected with said housing for filling said reservoir, said fill means comprising:
      (i) a container subassembly receivable within said internal chamber of said elongated housing, said container subassembly including:
         a. a container having a fluid chamber having first and second ends;
         b. displacement means movable relative to said fluid chamber for dispensing fluid from said chamber; and
         c. closure means for closing said second end of said fluid chamber of said container, said closure means including connector means for interconnecting said fluid chamber of said container with a source of fluid.

2. The fluid delivery device as defined in claim 1 in which said connector means includes a septum sealably connected to said container, said septum being pierceable by a cannula.

3. The fluid delivery device as defined in claim 1 in which said connector means includes a luer connector connected to said container.

4. The fluid delivery device as defined in claim 1 further including infusion means connected to said housing and being in fluid communication with said reservoir for infusing medicinal fluids into a patient.

5. The fluid delivery device as defined in claim 1 further including second fill means connected to said housing for introducing fluids into said reservoir.

6. The fluid delivery device as defined in claim 5 in which said second fill means comprises a luer connector affixed to said housing and a means for controlling fluid flow toward said reservoir.

7. A fluid delivery device having a fluid delivery passageway, said apparatus comprising:
   (a) an elongated housing having walls defining an internal chamber;
   (b) a support assembly connected to said housing and including an elongated body disposed within said internal chamber, said body having a receiving chamber, a pusher member disposed within said receiving chamber and an inlet passageway and an outlet passageway, said outlet passageway being in communication with said fluid delivery passageway;
   (c) an elongated tubular shaped elastomeric member connected proximate its ends to said elongated body, said elastomeric member having a central portion disposed within said internal chamber of said housing and overlaying said inlet and outlet passageways, said central portion of said elastomeric member being distendable by fluid flowing through said first fluid passageway from a first position in proximity with said support to a second position to form a fluid reservoir;
   (d) fill means interconnected with said housing for filling said reservoir, said fill means comprising:
      (i) a container subassembly receivable within said internal chamber of said elongated housing, said container subassembly including:
         a. a container having a fluid chamber having first and second ends;
         b. displacement means movable relative to said fluid chamber for dispensing fluid from said chamber; and
         c. closure means for closing said second end of said fluid chamber of said container, said closure means including a closure subassembly connected to said second end of said container, said closure subassembly comprising a housing, a closure panel hingedly connected to said housing and connector means for interconnecting said fluid chamber of said container with a source of fluid.

8. The fluid delivery device as defined in claim 7 in which said connector means includes a septum connected to said container, said septum being pierceable by a cannula.

9. The fluid delivery device as defined in claim 7 in which said connector means includes a luer connector connected to said container.

10. The fluid delivery device as defined in claim 7 further including second fill means connected to said housing for introducing fluids into said reservoir.

11. The fluid delivery device as defined in claim 7 in which said displacement means of said container subassembly includes a plunger having a pierceable wall and in which said support assembly includes a piercing cannula for piercing said pierceable wall of said plunger, said piercing cannula being in communication with said inlet to said reservoir.

12. The fluid delivery device as defined in claim 7 in which said closure means further comprises valve means for controlling fluid flow toward said chamber of said container.

13. The fluid delivery device as defined in claim 7 further including flow control means in communication with said reservoir for controlling fluid flow toward said infusion means.

14. The fluid delivery device as defined in claim 13 in which said flow control means comprises a fluid rate control member.

15. The fluid device as defined in claim 13 in which said flow control means comprises a filter.

16. A fill assembly for filling the fluid reservoir of a fluid delivery device, said fill assembly comprising a container subassembly connected to said fluid delivery device, said container subassembly including:

(a) a container having a fluid chamber having first and second ends;

(b) displacement means movable relative to said fluid chamber for dispensing fluid from said chamber; and (c) closure means for closing said second end of said fluid chamber of said container, said closure means including a closure subassembly connected to said second end of said container and connector means for interconnecting said fluid chamber of said container with a source of fluid.

17. The fill assembly as defined in claim 16 in which said closure subassembly further comprises a housing and a closure panel hingedly connected to said housing.

18. The fill assembly as defined in claim 16 in which said closure subassembly further comprises a threaded closure cap.

19. The fill assembly as defined in claim 16 in which said connector means includes a septum connected to said container, said septum being pierceable by a cannula.

20. The fill assembly as defined in claim 16 in which said connector means includes a luer connector connected to said container.

21. The fluid delivery device as defined in claim 16 in which said displacement means of said container subassembly includes a plunger having a pierceable wall.

22. The fill assembly as defined in claim 16 in which said connector means comprises a slit septum pierceable by a blunt end cannula.

23. The fill assembly as defined in claim 16 in which said container subassembly further includes a porous, self-venting closure removably connected to said first end of said container.

* * * * *